United States Patent
Ott et al.

(10) Patent No.: US 11,542,230 B2
(45) Date of Patent: Jan. 3, 2023

(54) CATALYSTS FOR THE SYNTHESIS OF ALKANESULFONIC ACIDS

(71) Applicant: BASF SE, Ludwigshafen am Rhein (DE)

(72) Inventors: Timo Ott, Duisburg (DE); Ingo Biertuempel, Duisburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/965,039

(22) PCT Filed: Feb. 13, 2019

(86) PCT No.: PCT/EP2019/053537
§ 371 (c)(1),
(2) Date: Jul. 27, 2020

(87) PCT Pub. No.: WO2019/158577
PCT Pub. Date: Aug. 22, 2019

(65) Prior Publication Data
US 2020/0369604 A1    Nov. 26, 2020

(30) Foreign Application Priority Data
Feb. 16, 2018    (EP) ..................... 18157127

(51) Int. Cl.
C07C 315/04     (2006.01)
C07C 303/06     (2006.01)
C07C 309/04     (2006.01)

(52) U.S. Cl.
CPC .......... C07C 315/04 (2013.01); C07C 303/06 (2013.01); C07C 309/04 (2013.01)

(58) Field of Classification Search
None
See application file for complete search history.

(56) References Cited

U.S. PATENT DOCUMENTS

| | | | |
|---|---|---|---|
| 2,493,038 A | 1/1950 | Snyder et al. | |
| 2005/0070614 A1 | 3/2005 | Richards | |
| 2006/0100458 A1* | 5/2006 | Sen | C07C 303/02 562/98 |
| 2016/0289176 A1 | 10/2016 | Ott et al. | |
| 2016/0289181 A1 | 10/2016 | Ott et al. | |
| 2019/0276394 A1* | 9/2019 | Dubois | C07C 303/06 |

FOREIGN PATENT DOCUMENTS

| | | | |
|---|---|---|---|
| CN | 1732141 A | 2/2006 | |
| CN | 105705486 A | 6/2016 | |
| CN | 105722819 A | 6/2016 | |
| CN | 105980352 A | 9/2016 | |
| WO | WO-2004041399 A2 * | 5/2004 | ............... C01B 3/34 |
| WO | WO 2007/136425 A2 | 11/2007 | |
| WO | WO 2015/071365 A1 | 5/2015 | |
| WO | WO 2015/071455 A1 | 5/2015 | |

OTHER PUBLICATIONS

Mukhopadhyay ("Direct Sulfonation of Methane at Low Pressure to Methanesulfonic Acid in the Presence of Potassium Peroxydiphosphate as the Initiator" Organic Process Research and Development, 2003, 7, p. 161-163) (Year: 2003).*
Wikipedia entry for Peroxymonosulfuric Acid, downloaded from https://en.wikipedia.org/wiki/Peroxymonosulfuric_acid on Aug. 12, 2021 (Year: 2021).*
Oxone® MSDS, downloaded from https://www.sigmaaldrich.com/US/en/product/sial/911356 on Mar. 1, 2022 (Year: 2022).*
Potassium persulfate (K2S2O8) MSDS, downloaded from https://www.sigmaaldrich.com/US/en/product/sial/906735 on Mar. 1, 2022 (Year: 2022).*
Potassium peroxydiphosphate (K4P2O8), downloaded from https://www.masterflex.com/i/acros-organics-ac343960250-potassium-peroxydiphosphate-25g/8831274 on Mar. 1, 2022 (Year: 2022).*
Flanagan ("The Active Principle of Caro's Acid, HSO5-: X-Ray Crystal Structure of KHSO5•H2O" J. Chem. Soc., Chem. Commun, 1984, p. 1574-1575) (Year: 1984).*
Oxone®, monopersulfate compound, downloaded from https://www.sigmaaldrich.com/US/en/product/sial/228036 on Mar. 1, 2022 (Year: 2022).*
International Search Report dated Apr. 9, 2019 in PCT/EP2019/053537 filed Feb. 13, 2019.
Mukhopadhyay, et al., "Synthesis of methanesulfonic acid and acetic acid by the direct sulfonation or carboxylation of methane", Studies in Surface Science and Catalysis, vol. 147, 2004, pp. 523-528.

* cited by examiner

*Primary Examiner* — Amy C Bonaparte
(74) *Attorney, Agent, or Firm* — ArentFox Schiff LLP

(57) ABSTRACT

The present invention relates to novel uses of stable inorganic peroxoacids as catalysts in the preparation of alkanesulfonic acids from alkanes and sulfur trioxide, methods for the production of alkanesulfonic acids employing said catalysts as well as reaction mixtures comprising said catalysts. The invention particularly relates to the production of methanesulfonic acid from methane and sulfur trioxide employing stable inorganic peroxoacids as catalysts.

8 Claims, No Drawings

CATALYSTS FOR THE SYNTHESIS OF ALKANESULFONIC ACIDS

The present invention relates to novel uses of stable inorganic peroxoacids as catalysts in the preparation of alkanesulfonic acids from alkanes and sulfur trioxide, methods for the production of alkanesulfonic acids employing said catalysts as well as reaction mixtures comprising said catalysts. The invention particularly relates to the production of methanesulfonic acid from methane and sulfur trioxide employing stable inorganic peroxoacids as catalysts.

Alkanesulfonic acids are organic acids that can reach a similar acid strength as that of inorganic mineral acids, for example, sulfuric acid. However, in contrast to usual mineral acids such as sulfuric and nitric acids, the sulfonic acids are non-oxidizing and do not give off vapors that are harmful to health, as can be observed with hydrochloric and nitric acids. Further, many sulfonic acids, for example, methanesulfonic acid, are biologically degradable. The applications of sulfonic acids are many, for example, in cleaning agents, surfactants, galvanic and electronic industry, as catalysts, and in organic synthesis, pharmaceutical chemistry, for example, as protective groups. The salts of sulfonic acids are employed, for example, as surfactants, for example, sodium dodecylsulfonate, or in the electroplating industry, especially as tin, zinc, silver, lead and indium, but also other metal, alkyl-sulfonates. Furthermore, organic salts are employed in pharmaceutical chemistry. The very high solubility of alkyl sulfonates plays an important role, in particular. Further, no harmful gases are formed in electrolysis, and the use of toxic compounds, for example, cyanide, which is common in many cases, is dispensed with.

The structurally simplest representative of alkanesulfonic acids is methanesulfonic acid. U.S. Pat. No. 2,493,038 describes the preparation of methanesulfonic acid from $SO_3$ and methane. US 2005/0070614 describes further methods for preparing methanesulfonic acid, and its application. The methods known in the prior art are in part complicated, cost-intensive, and lead to undesirable products because of the harsh reaction conditions.

The reaction conditions in conventional processes of alkanesulfonic acid production can result in undesirable side products, which even manifest themselves as disturbing inhibitors in the production of alkanesulfonic acids. This may lead to termination of the actual reaction for preparing the alkanesulfonic acid, but also to impurities, formation of side products and poor yields, based on sulfur trioxide and methane.

WO 2007/136425 A2 discloses the use of the compound di(methanesulfonyl) peroxide (DMSP), which must be prepared by a complex electrolysis and, in addition, is a crystallizable highly explosive solid, as an initiator in a reaction in which methanesulfonic acid is formed from sulfur trioxide and methane.

WO 2015/071365 A1 and WO 2015/071455 A1 both describe processes for the sulfonation of alkanes. The main steps are:
1) Synthesis of an initiator/initiator-solution.
2) Preparation of a sulfur trioxide-solution (oleum) by dissolving sulfur trioxide in an inert solvent (e.g. sulfuric acid)
3) Reaction of oleum with the corresponding alkane after or during addition of the initiator/initiator-solution in a high-pressure-reactor.
4) Quenching of non-reacted starting material
5) Purification (e.g. distillation, crystallization etc.)
6) Recycling of the inert solvent (e.g. sulfuric acid).

According to said prior art, the initiator is particularly prepared by reacting an alkanesulfonic acid R—$SO_3$H, i.e. the desired product, with hydrogen peroxide in order to form an initiator-precursor R—$SO_2$—O—OH. Said initiator-precursor is then reacted with $SO_3$ yielding initiator compounds such as R—$SO_2$—O—$SO_3$H. The cited prior art therefore requires some amount of the desired product to form an initiator.

It is thus the object of the present invention to provide novel catalysts for the homogeneous catalysis in the preparation of alkanesulfonic acids, especially methanesulfonic acid (MSA). Particularly, it is the object of the invention to provide catalysts that do not require the desired product itself to be present as an initiator-precursor. Further, requirements for sulfurtrioxide and alkanes should be of no relevance, meaning that not only absolute pure raw materials might be used, but that impurities do not affect negatively the reaction.

In a first embodiment, the object of the present invention is solved by the use of a compound comprising at least one inorganic peroxoacid or a salt thereof, wherein the peroxoacid is stable at room temperature, as a catalyst in the preparation of alkanesulfonic acids from alkanes and sulfur trioxide, especially in the preparation of methanesulfonic acid from methane and sulfur trioxide. Particularly, methane, ethane, propane, butane, isopropane, isobutane or a higher alkane can be reacted with sulfur trioxide to form the corresponding alkanesulfonic acid.

Surprisingly, it has been found that stable inorganic peroxoacids show a similar catalytic activity as peroxoacids derived from the desired alkanesulfonic acids. Therefore, the desired product is not required as a precursor of the catalyst. In principal, any inorganic peroxoacid, which is stable at room temperature, can be employed. Such inorganic peroxoacids or their corresponding oxoacids are cheaply available from commercial distributors.

Stability at room temperature is particularly to be understood as stability in a reaction solvent comprising sulfur trioxide and an alkane, especially methane. This solvent may be sulfuric acid. The peroxoacid according to the invention must be stable enough in order to act as catalyst in the production of alkanesulfonic acids and not to decompose.

Said decomposition may particularly take place by the release of reactive oxygen species such as superoxide anions ($O_2^-$). In this sense, stability of the peroxoacid catalysts of the present invention for example means the absence of the release of reactive oxygen species such as superoxide anions.

According to the invention, the peroxoacid is used as a catalyst in a condensed-phase homogeneous process. The peroxoacid catalyst is solved in the same phase as the reactants, i.e., an alkane and sulfur trioxide.

In the following, the assumed catalytic cycle is exemplary described for the employment of methane as alkane. The same catalytic cycle is assumed to apply to other alkanes. In general, the peroxoacid according to the invention can be described by the formula R—O—O—H. Without the intention of being bound by theory, it is assumed that the peroxoacid acts by activating sulfur trioxide towards the reaction with an alkane.

In a first step, the peroxoacid reacts with sulfur trioxide upon which an activated form of sulfur trioxide is formed:

R—O—O—H+$SO_3$->R—O—O—$SO_3$H    (R1)

In a second step, said activated form is able to react with methane in order to form methanesulfonic acid upon which the peroxoacid is regenerated:

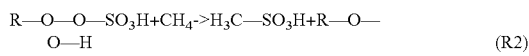

R—O—O—SO₃H+CH₄ -> H₃C—SO₃H+R—O—O—H  (R2)

In what follows, the present invention is described in its preferred embodiments. The description is meant to be exemplary and not to limit the scope of the invention.

In a preferred embodiment the peroxoacid comprises at least one peroxoacid of boron, silicon, phosphorus, carbon, nitrogen or sulfur. Any suitable peroxoacid of said elements can be used. The peroxoacids are typically derived from the corresponding oxoacid of the respective element.

Preferably, the peroxoacid used as a catalyst according to the invention is obtainable by a reaction of the corresponding oxoacid with a peroxide. More preferably, the peroxoacid is obtainable by a reaction of the corresponding oxoacid with hydrogen peroxide. Without the intention of being bound by theory, the reaction of an oxoacid with hydrogen peroxide can for example be described by

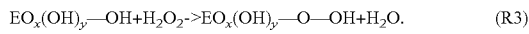

$EO_x(OH)_y$—OH+$H_2O_2$ -> $EO_x(OH)_y$—O—OH+$H_2O$.  (R3)

In a preferred embodiment, the peroxoacid used according to the invention comprises a polyprotic acid. Particularly, the peroxoacid may consist of one or more polyprotic acids. Said polyprotic peroxoacid comprises one or more peroxy groups, which can be described by —O—O—X, wherein X may be hydrogen and/or an alkaline and/or alkaline-earth metal. More preferably X is hydrogen, lithium, sodium and/or potassium. Most preferably, X is hydrogen.

Preferably, if a polyprotic acid is used, the peroxoacid comprises one or more hydroxyl groups in addition to the one or more peroxy groups. Said hydroxyl groups may be present in form of a salt, i.e., the groups can be described by —O—X, wherein X may be hydrogen, an alkaline metal and/or an alkaline-earth metal. Most preferably X is hydrogen. The replacement of hydrogen with an alkaline-(earth) metal, however, may be particularly necessary to stabilize the peroxoacid as required by the invention.

In a preferred embodiment of the invention, the reaction product of phosphoric acid ($H_3PO_4$) with hydrogen peroxide, the reaction product of boric acid ($H_3BO_3$) with hydrogen peroxide and/or potassium peroxomonosulfate ($KHSO_5$) is used as stable inorganic peroxoacid according to the invention. Surprisingly, it has been found that said preferred peroxoacids are particularly suitable as catalyst in the preparation of alkanesulfonic acids from alkanes and sulfur trioxide.

In an alternative embodiment, the object of the invention is solved by the use of a mixture comprising hydrogen peroxide and an inorganic oxoacid as catalyst in the preparation of alkanesulfonic acids from alkanes and sulfur trioxide, especially in the preparation of methanesulfonic acid from methane and sulfur trioxide. Optionally the mixture may comprise a solvent.

The oxoacid used in the mixture according to the invention must be suitable to yield a stable peroxoacid upon the reaction with hydrogen peroxide. In this alternative embodiment, the catalyst compound is produced in situ in the reaction mixture. Particularly suitable oxoacids comprise oxoacids of boron, silicon, phosphorus and/or sulfur.

The oxoacid may be a monoprotic or a polyprotic acid. Particularly, if a polyprotic acid is used, only a part of the hydroxyl groups may be replaced by peroxy groups upon the reaction with hydrogen peroxide. Preferably, boric acid ($H_3BO_3$) and/or phosphoric acid ($H_3PO_4$) are used in a mixture according to the invention.

In an alternative embodiment, the object of the invention is solved by a process for the preparation of alkanesulfonic acids from alkanes and sulfur trioxide comprising the steps of i) providing sulfur trioxide;
ii) reacting the sulfur trioxide with an alkane, especially methane, in a high-pressure autoclave or laboratory reactor;
iii) setting a pressure of from 1 to 200 bar;
iv) introducing an inorganic stable peroxoacid or a salt thereof;
v) controlling the temperature of the reaction mixture at 0° C. to 100° C.;
vi) if necessary purifying the reaction product, for example, by distillation or extraction.

The inventive process differs from similar processes from the prior art in that in step iv) an inorganic stable peroxoacid is added as catalyst. Said peroxoacid corresponds to the abovementioned peroxoacids which may be used as catalysts.

Sulfur trioxide may be provided in the form of oleum, i.e., a solution of sulfur trioxide in sulfuric acid. Instead of oleum also pure sulfur trioxide can be employed. This avoids the preparation of sulfur trioxide solutions. The reaction conditions are here without added solvents. Further, non-reacted sulfur trioxide can evaporate, avoiding the necessity of quenching it.

In a further embodiment, sulfur trioxide is used in a form of oleum with a trioxide content of 50% (w/w) or less, or 65% (w/w) or more. Surprisingly it has been found that for the processes of the present invention also oleum with a sulfur trioxide content of 65% (w/w) or more, especially of 70% w/w or more can be used without negatively affecting the inventive process. Even pure sulfur trioxide (100% (w/w) sulfur trioxide) may be used.

Due to the advantages being connected with the use of pure sulfur trioxide mentioned above, the use of pure sulfur trioxide is preferred in the process for manufacturing alkanesulfonic acids according to the present invention. As contrary to the prior art, a circulation of solvent is not necessary, alkanes comprising higher amounts of impurities compared to the prior art can be used. Impurities usually are enriched in the solvent leading to a reduced yield of alkanesulfonic acids. By avoiding solvents and thus a circulation of them, impurities originating from the alkanes are not negatively influencing the production of alkanesulfonic acids when pure sulfur trioxide is employed.

Sulfur trioxide, especially pure sulfur trioxide is reacted with an alkane in a reactor. For alkanes with a low boiling point, the use of a high-pressure reactor is necessary. For pentane and higher alkanes, a common laboratory reactor is sufficient. In the case of gaseous alkanes, for example, methane, a pressure of 1 to 200 bar gas pressure is set.

Subsequently, the peroxoacid catalyst according to the present invention is added. The catalyst may be provided in pure form or solved in a suitable solvent. Preferably, the initial molar ratio between the catalyst and $SO_3$ is in the range of 1:50 to 1:10000, more preferably 1:100 to 1:500, particularly 1:150. The catalyst may be provided in a solvent, particularly in sulfuric acid.

After the reaction has taken place, the reaction mixture contains essentially of the respective alkanesulfonic acid, especially methanesulfonic acid, as well as sulfuric acid. This mixture of alkanesulfonic acid, especially methanesulfonic acid (MSA), and $H_2SO_4$ might afterwards be used as the respective mixture. The combination of an alkanesulfonic acid, especially methanesulfonic acid, and sulfuric acid provides a strong acid in which even gold might be dissoluted enabling different fields of technical applicability.

Alternatively, the alkanesulfonic acid, especially MSA, might be separated i.e. the method of the invention comprises the optional step of the purifying the reaction product, which might be done by distillation or extraction.

But also alkanesulfonic acids, and specially methanesulfonic acids, might be used in different technical fields, i.e. as cleaning agent (cleaning comprising the area of cleaning and caring, home care as well as industrial and institutional cleaning of hard and soft surfaces, i.e. in dishwashing, commercial laundry, cleaning and sanitation, vehicle and transportation care, concrete cleaning, membrane cleaning, and others), for regeneration of ion exchange resins, in galvanic proceedings, in the area of oil, gas, mining, treatment of metals and/or their surfaces, in different areas of pharmaceutical, chemical and argro-chemical industry or in the production of biodiesel. MSA might also be used in galvanization process of plastics, the broad area of batteries, such as lead battery recycling and recycling in general, such as metal recycling, as well as borane generation are further possible areas of application.

In an alternative embodiment, the object of the invention is solved by a process for the preparation of alkanesulfonic acids from alkanes and sulfur trioxide comprising the steps of
i) providing sulfur trioxide;
ii) reacting the sulfur trioxide with an alkane, especially methane, in a high-pressure autoclave or laboratory reactor;
iii) setting a pressure of from 1 to 200 bar;
iv) introducing an inorganic oxoacid or a salt thereof and hydrogen peroxide, wherein the oxoacid and the hydrogen peroxide are introduced sequentially or simultaneously;
v) controlling the temperature of the reaction mixture at 0° C. to 100° C.;
vi) if necessary purifying the reaction product, for example, by distillation or extraction.

The process according to this embodiment of the invention differs from the aforementioned embodiment of the inventive process in that the catalyst is employed by introducing an oxoacid and hydrogen peroxide rather than a peroxoacid. The peroxoacid is thus formed in situ in the autoclave or laboratory reactor in which the reaction of sulfur trioxide and the alkane takes place. Any suitable oxoacid which can be used in a catalyst mixture in the preparation of alkanesulfonic acids as defined above can be employed. Accordingly, the oxoacid needs to be capable of forming a stable peroxoacid.

Particularly suitable oxoacids comprise oxoacids of boron, silicon, phosphorus and/or sulfur. The oxoacid may be a monoprotic or a polyprotic acid. Particularly, if a polyprotic acid is used, only a part, especially only one, of the hydroxyl groups may be replaced by peroxy groups upon the reaction with hydrogen peroxide. Preferably, boric acid ($H_3BO_3$) and/or phosphoric acid ($H_3PO_4$) are employed.

Both the oxoacid and hydrogen peroxide are added to the reactor. They can be added in a mixture, optionally with a solvent. Suitable solvents comprise sulfuric acid or a liquid alkanesulfonic acid, e.g. methanesulfonic acid. The oxoacid and hydrogen peroxide may also be added separately or simultaneously. If both compounds are added separately, each may optionally be solved in a solvent, for example sulfuric acid. In yet another alternative, both compounds may be added sequentially, wherein each compound may be added as the first or the second compound.

Preferably, the oxoacid and hydrogen peroxide are added in a molar ratio of 1:5 to 5:1, more preferably in a molar ratio of 1:2 to 2:1, most preferably in a molar ratio of 1:1.

The initial molar ratio between the oxoacid and the $SO_3$ is preferably in the range of 1:50 to 1:10000, more preferably in the range of 1:100 to 1:500.

In an alternative embodiment, the object of the invention is solved by a mixture comprising an alkane, sulfur trioxide, a stable inorganic peroxoacid and optionally a solvent. The inventive mixture is capable of producing an alkanesulfonic acid. Particularly, if the mixture is set at a pressure of 1 to 100 bar and held at a temperature of 0 to 100° C., an alkanesulfonic can be produced in an efficient way. The stable inorganic peroxoacid acts as a catalyst.

In a preferred embodiment, the alkane is methane. Such a preferred mixture is capable of forming methanesulfonic acid.

In an alternative embodiment, the object of the invention is solved by a mixture comprising an alkane, sulfur trioxide, an inorganic oxoacid, hydrogen peroxide and optionally a solvent, wherein the inorganic oxoacid is capable of forming a stable inorganic peroxoacid. The inventive mixture is capable of producing an alkanesulfonic acid. Particularly, if the mixture is set at a pressure of 1 to 100 bar and held at a temperature of 0 to 100 ° C., an alkanesulfonic can be produced in an efficient way. The inorganic oxoacid and the hydrogen peroxide react to in situ form an inorganic stable peroxoacid, which is capable of acting as catalyst.

In a preferred embodiment, the alkane is methane. Such a preferred mixture is capable of forming methanesulfonic acid.

EXAMPLES

Example 1: Reaction Using Boronic Peroxide as Initiator

In a 3.75 L autoclave, 1000 g of 36% (w/w) oleum is charged, and the temperature controlled at 50° C. After a pressure of 100 bar of methane gas was set, intensive stirring is performed with a stirrer from the company Parr. Now, the initiator solution consisting of 100 ml sulfuric acid, 5.1 g boronic acid and 3.6 ml hydrogen peroxide (70%) is metered dropwise to the solution. The pressure drops to 34 bar within 4 hours. The yield is higher than 90%, based on sulfur trioxide. The reaction product contains 43% (w/w) methanesulfonic acid.

Example 2: Reaction Using Phosphoric Peroxide as Initiator

In a 3.75 L autoclave, 1000 g of 36% (w/w) oleum is charged, and the temperature controlled to 50° C. After a pressure of 100 bar of methane gas was set, intensive stirring is performed with a stirrer from the company Parr. Now, the initiator solution consisting of 100 ml sulfuric acid, 9,4 g phosphoric acid (85%) and 3.6 ml hydrogen peroxide (70%) is metered dropwise to the solution. The pressure drops to 30 bar within 4.5 hours. The yield is higher than 90%, based on sulfur trioxide. The reaction product contains 44% (w/w) methanesulfonic acid.

The invention claimed is:
1. A process of preparing an alkanesulfonic acid, the process comprising:
preparing a catalytic reaction product comprising a catalyst, wherein the catalyst comprises an inorganic peroxoacid or a salt thereof, and wherein preparing the catalytic reaction product comprises reacting an inorganic oxoacid with a peroxide to provide the catalyst in situ; and catalyzing a reaction of an alkane and sulfur trioxide with the catalytic reaction product, wherein the inorganic peroxoacid or salt thereof does not release superoxide anions of formula $O_2^-$ at room temperature in the presence of the alkane and sulfur trioxide.

2. The process of claim 1, wherein the inorganic peroxoacid comprises a peroxoacid of boron, silicon, phosphorus or sulfur.

3. The process of claim 1, wherein the inorganic peroxoacid comprises a polyprotic acid comprising a peroxy group —O—O—X, wherein X is H, Li, Na and/or K.

4. The process of claim 3, wherein the polyprotic acid further comprises a group —O—X, wherein X is H, Li, Na and/or K.

5. The process of claim 1, wherein the inorganic oxoacid comprises phosphoric acid and/or boric acid, and wherein the peroxide comprises hydrogen peroxide and/or potassium peroxomonosulfate.

6. The process of claim 1, comprising:
   i) providing the sulfur trioxide;
   ii) reacting the sulfur trioxide with the alkane in a high-pressure autoclave or laboratory reactor;
   iii) setting a pressure of from 1 to 200 bar;
   iv) introducing the catalytic reaction product;
   v) controlling a temperature of a reaction mixture at 0° C. to 100° C.; and
   vi) optionally purifying a reaction product.

7. The process of claim 6, wherein the alkane is methane and the alkanesulfonic acid is methanesulfonic acid.

8. The process of claim 1, wherein the alkane is methane and the alkanesulfonic acid is methanesulfonic acid.

* * * * *